(12) United States Patent
Hernik

(10) Patent No.: US 8,651,412 B2
(45) Date of Patent: Feb. 18, 2014

(54) DEVICE FOR HOLDING AN ELASTICALLY DEFORMABLE WINDING ARTICLE AND APPARATUS FOR WINDING THE WINDING ARTICLE INTO THE DEVICE

(75) Inventor: Matthias Hernik, Bad Urach (DE)

(73) Assignee: Endox Feinwerktechnik GmbH, Bad Urach (DE)

( * ) Notice: Subject to any disclaimer, the term of this patent is extended or adjusted under 35 U.S.C. 154(b) by 418 days.

(21) Appl. No.: 12/387,282

(22) Filed: Apr. 30, 2009

(65) Prior Publication Data

US 2009/0277988 A1 Nov. 12, 2009

(30) Foreign Application Priority Data

May 7, 2008 (DE) .......................... 10 2008 022 666

(51) Int. Cl.
*B65H 16/00* (2006.01)

(52) U.S. Cl.
USPC ........................................................ 242/588.3

(58) Field of Classification Search
USPC ............ 242/388.6, 388.9, 615.3, 588, 588.3, 242/588.6, 472.7, 613.3, 536, 537, 602.1, 242/602.3, 172; 206/63.3, 303, 364, 438, 206/702; 600/585
See application file for complete search history.

(56) References Cited

U.S. PATENT DOCUMENTS

| | | | |
|---|---|---|---|
| 2,711,734 A | | 6/1955 | Moe |
| 4,860,757 A | * | 8/1989 | Lynch et al. .................. 600/434 |
| 4,917,094 A | * | 4/1990 | Lynch et al. .................. 600/434 |
| 5,273,042 A | * | 12/1993 | Lynch et al. .................. 600/434 |
| 5,344,011 A | * | 9/1994 | DiBernardo et al. ......... 206/364 |
| 5,366,444 A | * | 11/1994 | Martin .......................... 604/159 |
| 5,507,300 A | * | 4/1996 | Mukai et al. .................. 600/585 |
| 5,827,202 A | * | 10/1998 | Miraki et al. ................. 600/585 |
| 6,086,008 A | | 7/2000 | Gray et al. |
| 7,766,162 B2 | * | 8/2010 | Maki et al. .................... 206/364 |
| 8,136,656 B2 | * | 3/2012 | Kennedy et al. ............. 206/63.3 |
| 8,256,613 B2 | * | 9/2012 | Kirsch et al. ................. 206/339 |
| 2009/0071851 A1 | * | 3/2009 | Maki et al. .................... 206/210 |

FOREIGN PATENT DOCUMENTS

| | | |
|---|---|---|
| DE | 705 802 C | 5/1941 |
| DE | 7330339 U | 8/1973 |
| DE | 28 45 629 A1 | 4/1979 |
| DE | 197 51 194 C1 | 5/1999 |
| DE | 10 2005 013 742 A1 | 5/2006 |
| EP | 0 050 606 A1 | 4/1982 |
| GB | 2 215 703 A | 9/1989 |
| WO | WO 97/11736 A1 | 4/1997 |
| WO | WO 2006/055865 A2 | 5/2006 |

* cited by examiner

*Primary Examiner* — Michael Mansen
*Assistant Examiner* — Juan Campos, Jr.
(74) *Attorney, Agent, or Firm* — Kriegsman & Kriegsman

(57) ABSTRACT

The invention relates to a device for holding an elastically deformable winding article, in particular a flexible medical instrument such as a medical guidewire or a catheter, with a winding article receptacle and with a housing part (14) covering the winding article receptacle at least in parts, which form a receptacle space for holding the winding article, the winding article receptacle and the housing part being connected to one another such that they are twistable relative to each other and a winding article guide being provided in the receptacle space, which winding article guide arranges a number of turns of the winding article next to each other when winding the winding article. (FIG. 2 is provided to this end)

11 Claims, 6 Drawing Sheets

Figure 1:
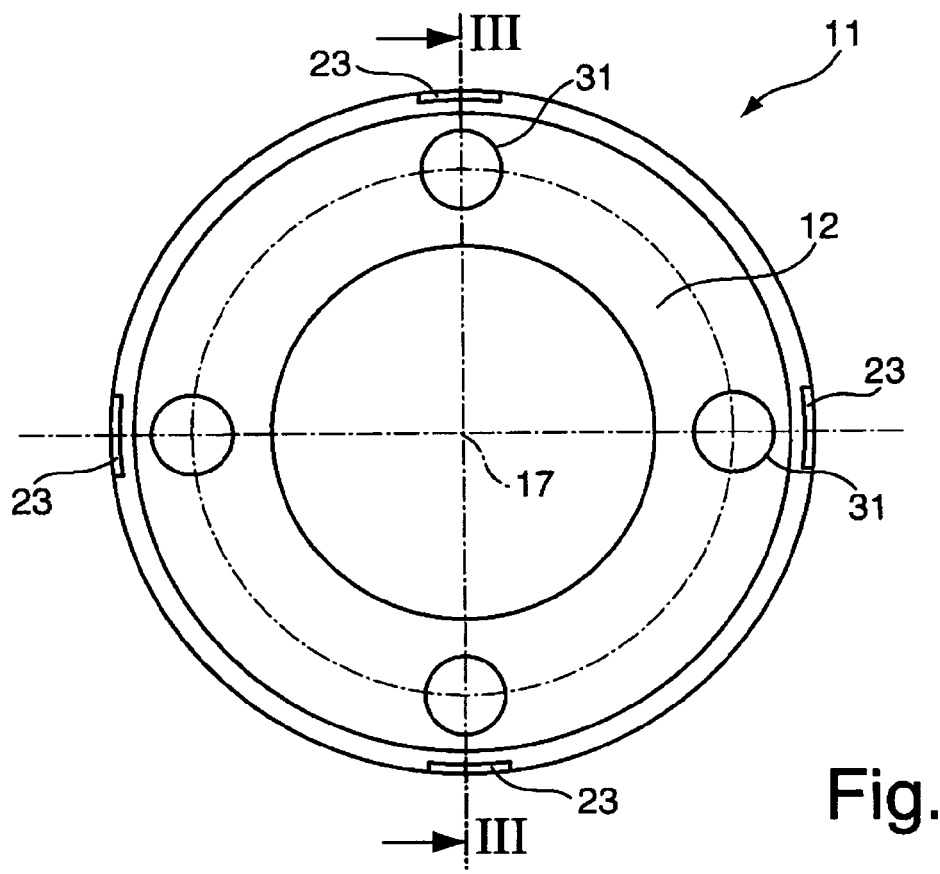

DEVICE FOR HOLDING AN ELASTICALLY DEFORMABLE WINDING ARTICLE AND APPARATUS FOR WINDING THE WINDING ARTICLE INTO THE DEVICE

The invention relates to a device for holding an elastically deformable winding article, in particular a flexible medical instrument such as a medical guidewire or a catheter, with a winding article receptacle and a housing covering the winding article receptacle at least in parts, which form a receptacle space for holding the winding article; and it also relates to an apparatus for winding the winding article into such devices.

DE 197 51 194 C1 discloses a wire dispenser for elastically deformable wires which comprises an annular element extending over a circumferential angle of over 180°, into which an elastically deformable wire can be inserted in a wound fashion. In order to insert the elastically deformable wire, such an annular element has an open cross-sectional profile with a wire insertion slit, which runs continuously along the circumferential direction and is formed lying radially on the inside. This wire insertion slit lying radially on the inside is covered at least in parts by a covering element which can be fixed in a detachable manner in the annular element in order to secure the elastically deformable wire in the annular element. An analogous arrangement is provided in the case of a wire insertion slit provided in a side flank of the annular element.

Such wire dispensers are provided for storing elastically deformable wires used in medicine, for example in catheterization. Such guidewires have a length of, for example, four meters. To make reliable and simple handling of the very thin wires possible, they are stored in such wire dispensers.

However, the apparatus known from DE 197 51 194 C1 has the disadvantage of the individual turns being arranged arbitrarily in the receptacle space of the annular element when the wire is inserted into a receptacle space of the annular element having a C-shaped cross section. Hence, there is a risk of the wire becoming entangled, particularly when the wire is quickly pulled from the wire dispenser, as a result of which further pulling off is no longer possible or requires a considerable amount of time.

The invention is therefore based on the technical object of providing a device and an apparatus for automatically winding the winding article in such devices, which can easily be refilled to be used again after the first use of a winding article, in particular a medical guidewire or a catheter, and which can subsequently be removed safely and quickly for continued use.

According to the invention, this object is achieved by the features of claim 1.

The device according to the invention, in particular for flexible medical instruments, has a winding article guide in the receptacle space which arranges a number of turns of the winding article next to one another whilst winding the winding article. As a result of this, one turn is placed next to the other one during the winding of the winding article into the receptacle space of the device or while the winding article is held in the receptacle space of the device so that an ordered winding arrangement is provided, as a result of which a quick removal of the winding article is made possible because one winding after another can be pulled off without influencing an adjacent turn. Such a winding receptacle which arranges every turn adjacent to the next turn can be operated in a simple manner as a result of the design of the winding article guide, so that filling the device is ensured and the individual turns are arranged next to one another in the receptacle space. The device is designed in particular for flexible medical instruments, such as medical guidewires, catheters, loops, biopsy forceps or the like.

In accordance with one preferred embodiment of the invention, provision is made for the winding article guide to be formed by a shaped surface, in particular a grooved surface, in the receptacle space, the shaped surface being formed by a groove. This makes it possible for the winding article held by the device to be provided in an ordered fashion in the receptacle space, by the one turn being placed next to the other turn. The shaped surface can afford the possibility of precise guiding and positioning of the winding article within the receptacle space.

A preferred refinement of the invention provides for a distance between a bearing surface of the housing part and an end surface of the encircling groove to be designed to be smaller than, in terms of its diameter, the smallest winding article to be held, in particular to be smaller than half of its diameter. This ensures that the individual turns in the individual compartments formed by the encircling groove do not lie against each other. Moreover, this advantageously affords the possibility of every turn being completely held in the encircling groove.

According to a further preferred refinement of the invention, provision is made for an effective height of the receptacle space to be designed to be smaller than twice the diameter of the winding article. The effective height comprises both the depth of the groove and the distance between the end face of the winding receptacle and the bearing surface on the housing part lying opposite it. This ensures that the turns of the winding article lying next to one another lie secured with respect to the shaped surface in the receptacle space so that entangling or crossing of individual turns is prevented.

For the purposes of threading the winding article on and off in a simple manner, provision is preferably made for the winding article receptacle and the housing part, which together form or surround the receptacle space, to be arranged such that they can twist relative to one another. This makes it possible to obtain a rapid winding or unwinding process by twisting one part or the other part or simultaneously twisting both parts of the device.

Provision is preferably made on the housing part for an insertion opening leading into the receptacle space. This can make it possible for the winding article to be drawn in and pulled out in a targeted manner. The insertion opening preferably extends over the entire receptacle space so that visual inspection with respect to the already wound winding article or the winding article still located in the device is made possible at the same time.

The insertion opening in the housing part preferably has an insertion bevel aligned with the receptacle space. This can make it possible to easily insert the winding article into the receptacle space without said article having kinks.

According to a further preferred refinement of the invention, provision is made for the winding article guide to the receptacle space, which guide is designed in particular as a grooved surface, to have a groove depth which comprises at least half of the winding article diameter. This makes it possible for every turn of the winding article to be securely held in the groove and kept therein. Adjacent turns are arranged separated from one another. Hence they cannot influence each other during the winding and unwinding.

According to a first advantageous embodiment of the invention, the receptacle space for holding the turns of the winding article arranged next to one another is aligned radially with respect to the axis of rotation of the winding article receptacle and of the housing part. In particular, the shaped surface of the winding article receptacle is designed radially with respect to the axis of rotation of the winding article receptacle and of the housing part. Such an embodiment has the advantage of providing a disc-shaped device, in particular a flat disc-shaped device, which has a small installation volume.

In an alternative refinement of the invention, provision is made for the receptacle space of the device to be aligned axially with respect to the axis of rotation of the winding article receptacle and of the housing part. This makes it possible to provide a compact, annular arrangement of the device which likewise makes simple handling possible.

The receptacle space of the device preferably has lobes which are arranged lying opposite the shaped surface and which preferably extend transversely with respect to the shaped surface. As a result of these lobes, the bearing surface of the winding article located in the receptacle space is significantly minimized. The winding article rests directly on the shaped surface and is kept in a resting position by the rotation of the winding article receptacle or of the housing part. The lobes in the receptacle space lie opposite the shaped surface. As a result of this, the handling during winding and unwinding can require less force and may be subject to reduced friction.

The winding article receptacle and the housing part which form the device are preferably connected to one another by a detachable latching connection. As a result of this, said parts can easily and quickly be disassembled and separated from one another for autoclaving. As a result of the preferred two-part embodiment of the device, simple and quick assembly without additional assisting instruments is possible after autoclaving.

In at least one of the two parts of the device, at least one resiliently yielding latching element is provided which engages on the other part and forms the detachable latching connection so that the two parts are fixedly assigned to one another, but are arranged such that they can twist relative to each other. By way of example, latching hooks can be provided for this purpose, which engage on a guiding surface of the other part lying opposite them. Likewise, provision can be made for latching lugs which engage in a recess of the other part and at the same time enable a rotational movement in the winding article receptacle relative to the housing part.

According to a further advantageous refinement of the invention, for the purposes of simple handling, at least one gripping surface, in particular a recessed grip, is provided on the housing part, the winding article receptacle or the housing part and the winding article receptacle. Hence, reliable actuation can be made possible.

Furthermore, a Luer connection or a rinsing opening is preferably provided on the housing part or the winding article receptacle. The receptacle space can easily be rinsed by means of such a Luer connection. This at the same time makes it possible to clean the winding article.

Furthermore, the object is achieved by an apparatus for winding an elastically deformable winding article, in particular flexible medical instruments, into a device, in particular in accordance with one of the preceding claims, by a rotation device which can be accessed from the outside being provided on a housing and said device having catches which engage into recessed grips or other recesses on a winding receptacle or on a housing part of the device, after fitting the device into the rotation device; by provision being made for at least one anti-twist protection, which is arranged on the housing and engages on the housing part or the winding receptacle; and by a drive device comprising a control and a motor driving a rotation device for winding the winding article into the device for holding the elastically deformable winding article. Such an apparatus makes automatic winding of an elastically deformable winding article into the device possible in an easy and quick fashion. In the process, the device is simply placed onto a rotation device or coupled with the latter and the winding article is positioned in the envisaged position with respect to the insertion opening of the receptacle space of the device and subsequently a rotation, preferably of the winding receptacle, is driven by starting the winding apparatus. Subsequently, the winding article is pulled into the receptacle space of the device, and the individual turns are arranged separately from one another in the receptacle space.

According to a further preferred refinement of this apparatus for winding an elastically deformable winding article, the rotation device comprises a rotary plate which is preferably provided in a receptacle recess in the housing. The device can preferably be arranged in the receptacle recess in an interlocking fashion and, in particular, is positioned in the receptacle recess by a detachable lock. The design of the receptacle recess, into which the rotation device is preferably integrated, allows the formation of a housing closed off to the outside. At the same time, the receptacle recess, whose shape is preferably matched to the outer contour of the device for winding an elastically deformable winding article, can provide anti-twist protection. In particular, provision is made for locks distributed radially over the periphery of the receptacle recess so that the device is kept down against the rotation device during the winding process. By way of example, these can be resilient latching elements.

A further preferred refinement of the apparatus provides for an ejector element or a recessed grip adjacent to the receptacle recess to be provided for removing the device from the receptacle recess. By way of example, such an ejector element can be integrated in the rotation device or in the receptacle recess. In this case, it is possible, for example, that a moveable or pivotable ejector element or a bolt or the like is actuated by a pushbutton on the housing so that the device can be released from the lock in the receptacle apparatus and can be removed. This ejector element can also be integrated into the catch by, for example, the catches being arranged such that they can move up and down with respect to the rotary plate of the rotation device so that ejection is made possible by means of a connecting link lying underneath, a slide or the like.

A further preferred embodiment of the apparatus provides an optical signalling device in the axis of rotation of the rotation device or outside of the receptacle recess, which signalling device is trimmed to the insertion opening of the receptacle space of the device for winding an elastically deformable winding article and can preferably be adjusted in the radial direction along the insertion opening. This optical signalling device can show the user the position of the insertion position, as a function of the length of the winding article, for winding the winding article. By way of example, this starting position can be set by a separate potentiometer of the apparatus so that for all subsequent winding processes a significant reduction in the time for equipping the device with a winding article is made possible. By way of example, the optical signalling device protrudes upwards with respect to the receptacle recess so that, for example, a coloured beam of light, in particular visible laser light, on the insertion opening is made possible for identifying the starting position of the winding process.

In accordance with a further preferred refinement of the apparatus, provision is made for the winding speed and/or the duration of winding a predetermined length of the winding article to be adjustable, in particular by means of a potentiometer. This makes it possible to match the drive speed, the feed of the drive speed and the winding duration of the apparatus to the winding article, so that in particular when holding different flexible medical instruments an appropriate winding speed can be set in each case. At the same time, the winding speed is a function of the winding length. Preferably, provision is made for one to three rotations, for example, to be driven with an increasing winding speed at the beginning of the winding process. Subsequently, a predetermined number of turns are wound at a high winding speed, and the last one to three turns are preferably again driven with an ever more decreasing winding speed.

Figure 2:
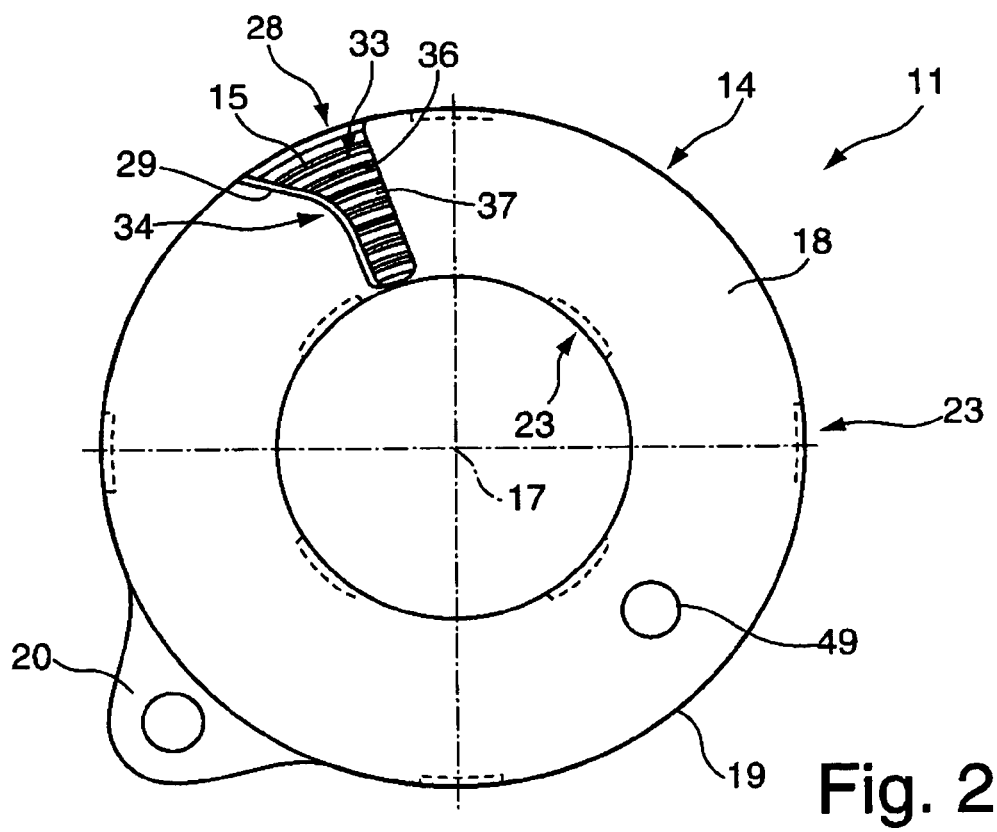
Figure 3:
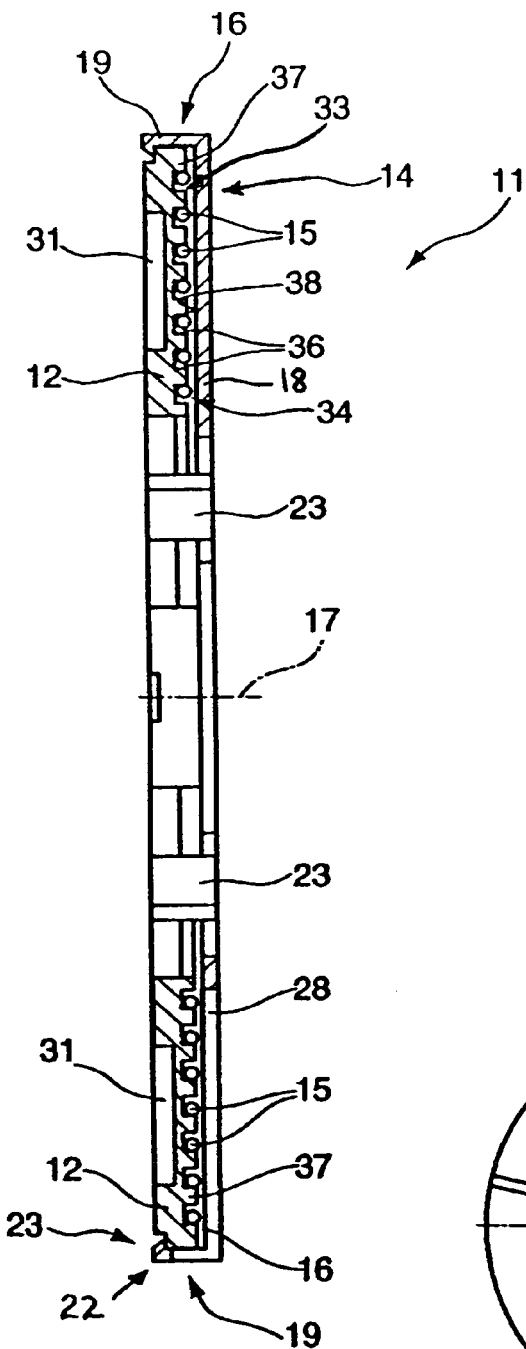
Figure 4:
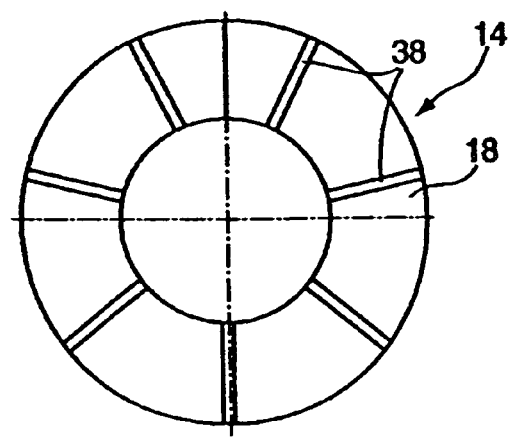
Figure 5:
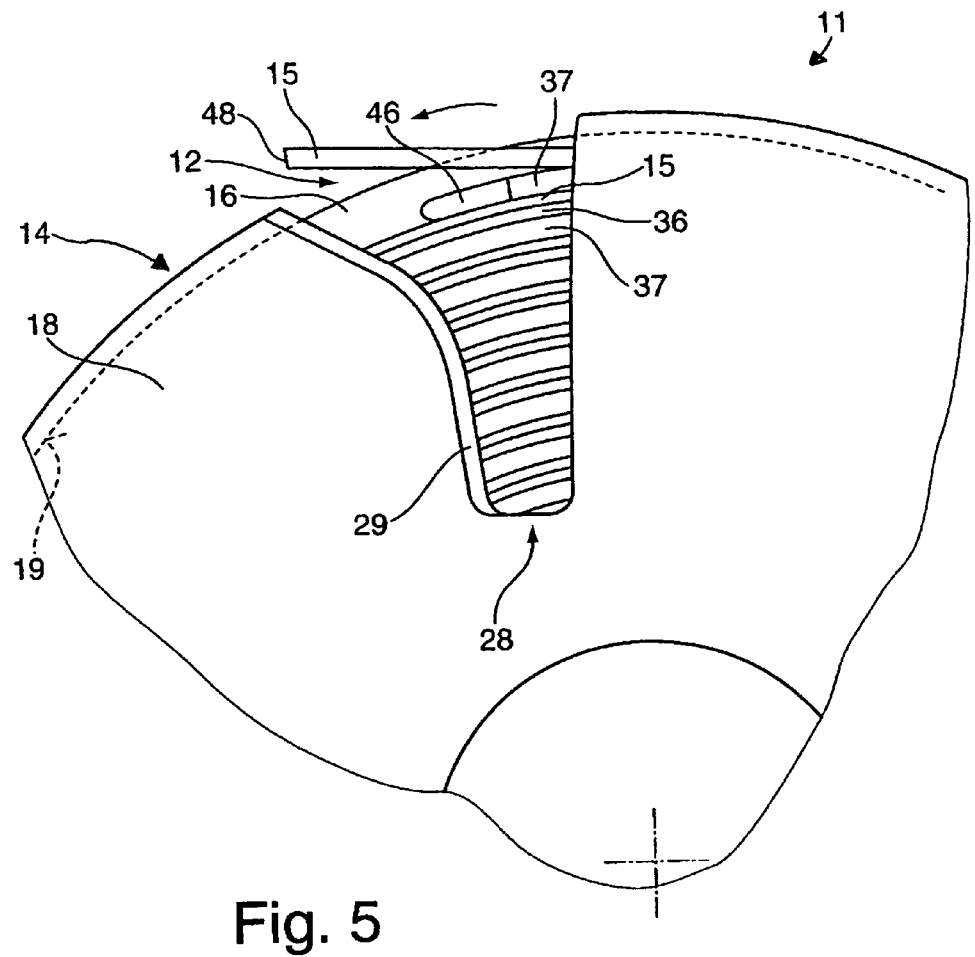
Figure 6:
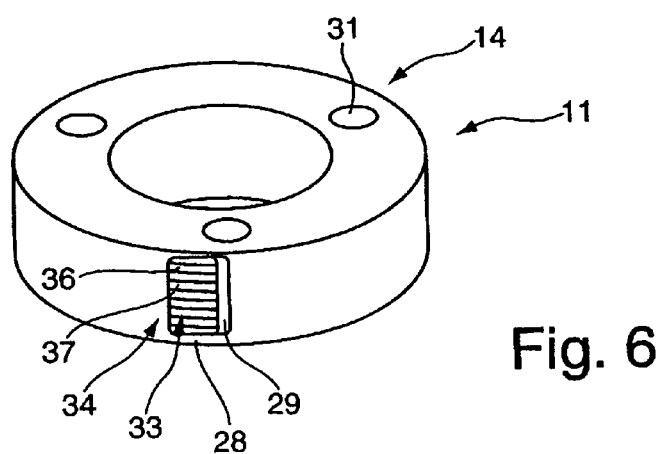
Figure 7A:
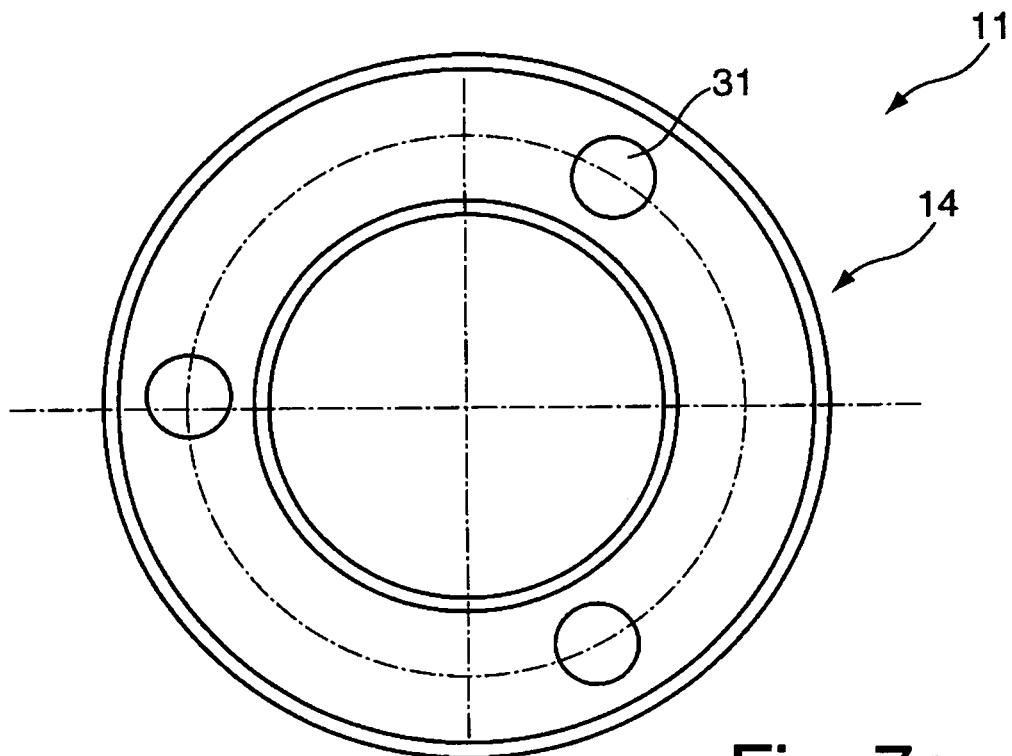
Figure 7B:
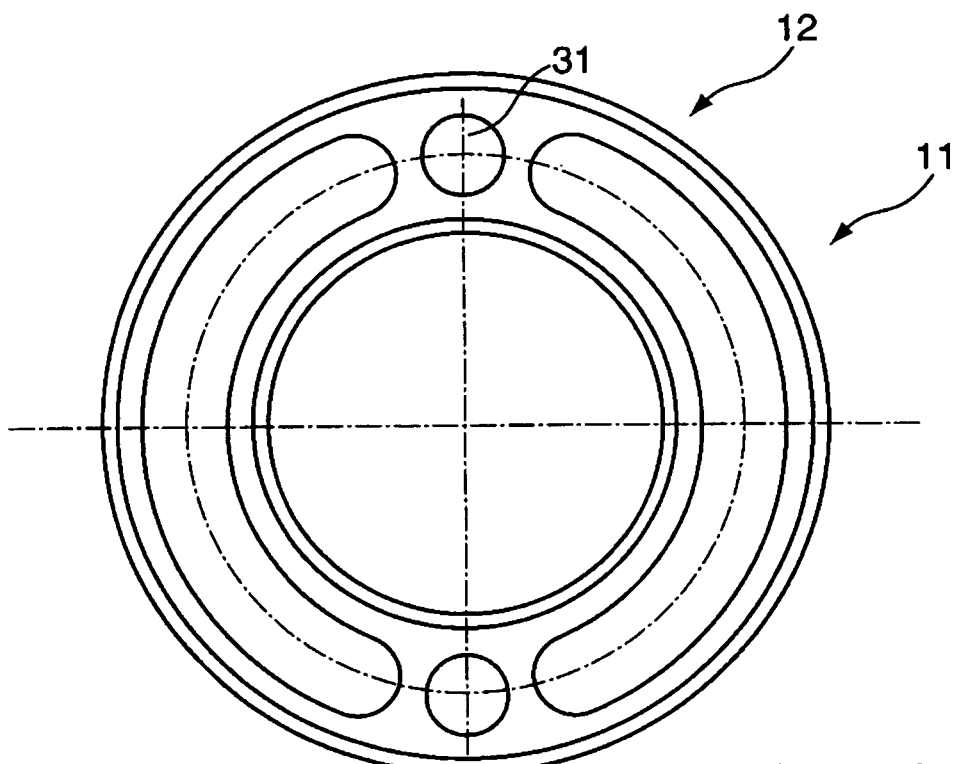
Figure 8:
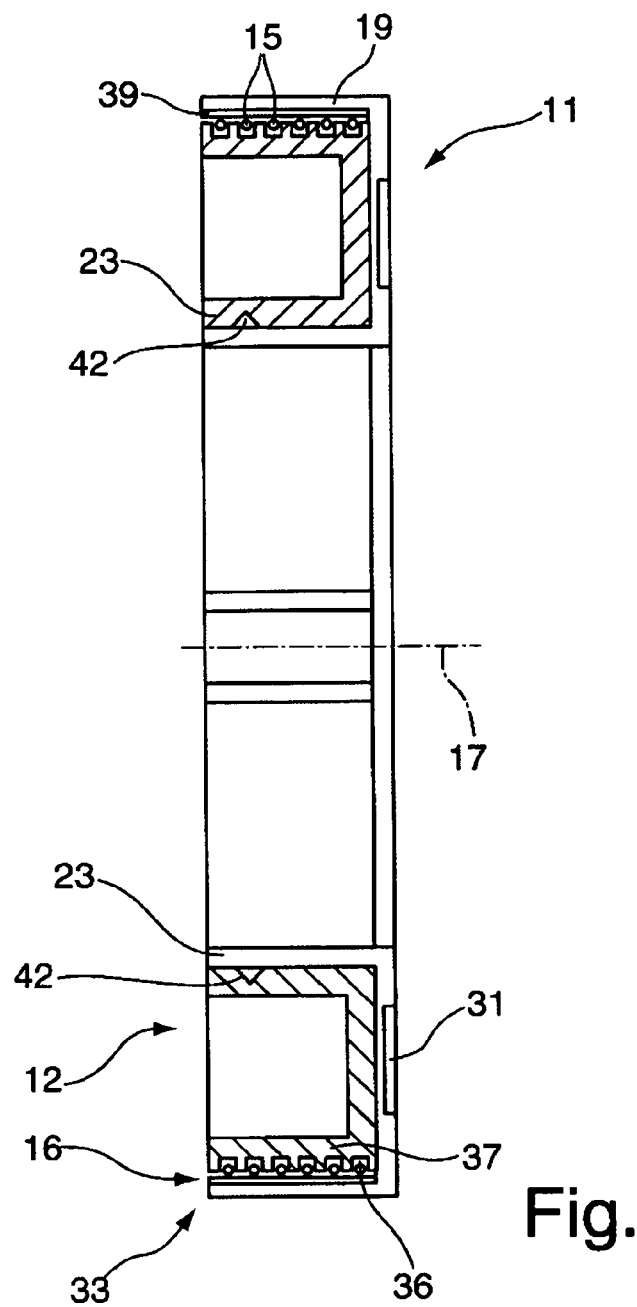
Figure 9:
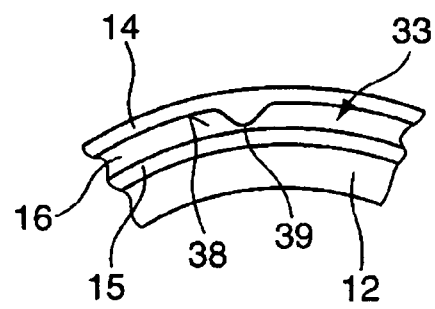
Figure 10:
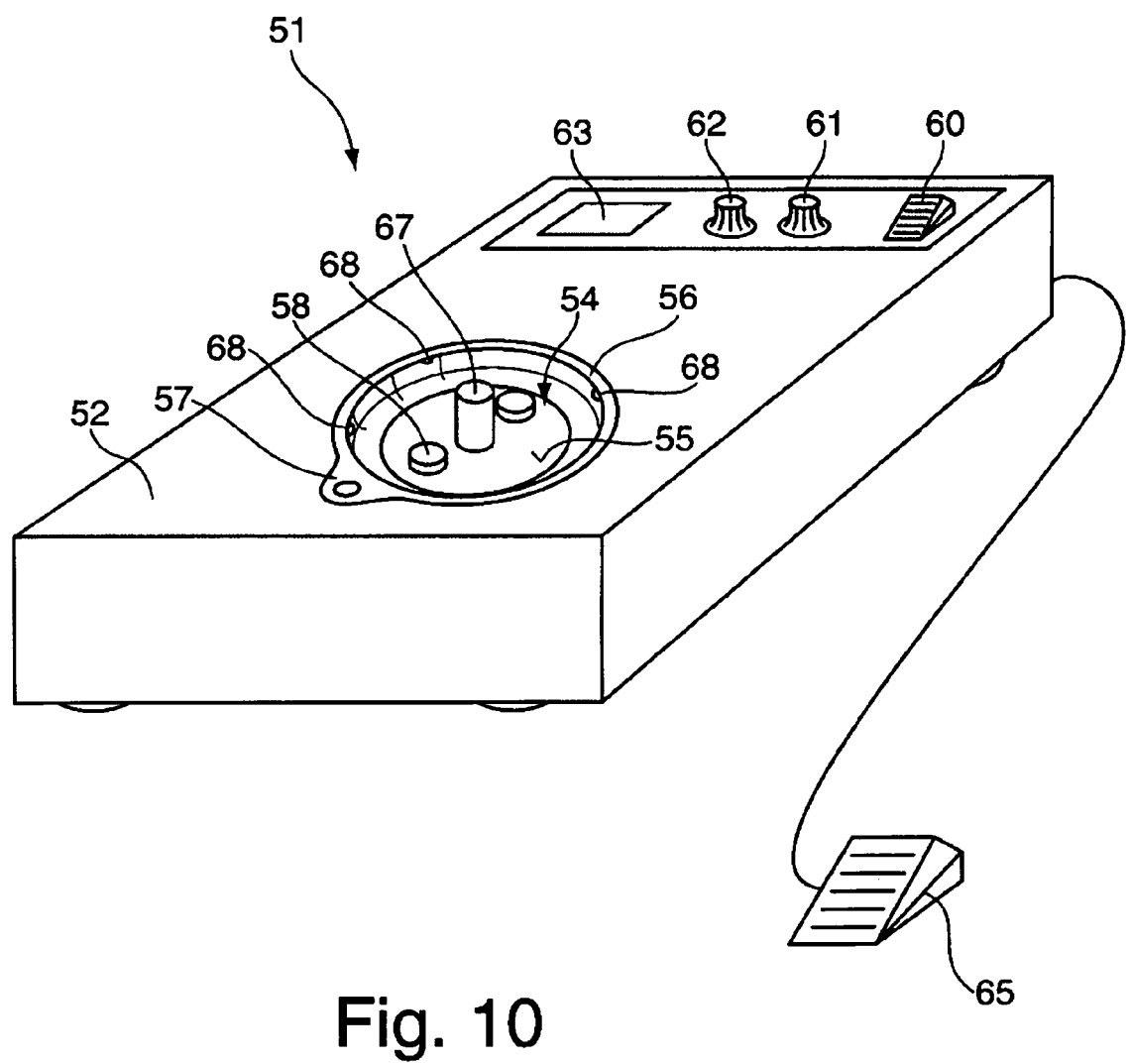

The invention and further advantageous embodiments and developments thereof are described in more detail and explained below, with reference to the examples illustrated in the drawings. The features which can be gathered from the description and the drawings can be applied according to the invention either individually or in groups in an arbitrary combination. In particular, FIG. 1 shows a first side view of a first embodiment of the device according to the invention, FIG. 2 shows a further side view of the device in accordance with FIG. 1, FIG. 3 shows a schematic sectional view of the device in accordance with FIG. 1, FIG. 4 shows a schematic view of a housing part of the device in accordance with FIG. 1, FIG. 5 shows a schematically enlarged view of an insertion opening on the housing part of the device in accordance with FIG. 1, FIG. 6 shows a perspective view of an alternative embodiment of the device according to the invention, FIG. 7a shows a first side view of the device in accordance with FIG. 6, FIG. 7b shows a further side view of the device in accordance with FIG. 6, FIG. 8 shows a schematic sectional view of the device in accordance with FIG. 6, FIG. 9 shows an enlarged section of a receptacle space of the device in accordance with FIG. 6, and FIG. 10 shows a perspective view of an apparatus for winding a winding article into the device in accordance with FIGS. 1 to 9.

FIG. 1 illustrates a first side view of a device according to the invention. FIG. 2 shows an opposite side of the device of FIG. 1. FIG. 3 illustrates a schematic full cut along the line III-III in FIG. 1.

The device preferably only consists of two parts and comprises a winding article receptacle and a housing part surrounding or covering the winding article receptacle at least in parts. An annular receptacle space 16 is formed between the winding article receptacle 12 and the housing part 14 and is provided for holding an elastically deformable winding article 15, in particular elastically deformable instruments such as a medical guidewire, a loop, biopsy forceps or a catheter or the like. This device is preferably used as a medical instrument dispenser.

The housing part 14 and the winding article receptacle 12 are arranged with respect to one another such that they can be twisted relative to one another about the axis of rotation 17. To this end, the housing part 14 has an annular base area 18 with an outer, radially extending lateral surface 19, within which the winding article receptacle 12, preferably designed as a disc-shaped annular element 21, can be arranged. The winding article receptacle 12 and the housing part 14 are connected to one another by a detachable latching connection 22. The lateral surface 19 of the housing part 14 comprises at least one latching element 23 in order to arrange the winding article receptacle 12 detachably with respect to the housing part 14. The latching element 23 is for example designed as a latching hook or a rear-engagement, which is integrally formed onto the base area 18 of the housing part 14. They can preferably engage on an outer shoulder or winding receptacle and fix the housing part 14 with respect to the winding receptacle 12 in its position. To ensure that the latching element 23 is designed to resiliently yield, provision can be made, for example, for U-shaped recesses in the base area 18 of the housing part 14. Such latching elements 23 can be provided on an outer lateral surface 19. These latching elements 23 can also be arranged on an inner periphery of the disc-shaped housing part 14. Additionally, the inner periphery can comprise a further lateral surface, analogous to the outer lateral surface 19, with it being possible for the latching elements 23 on the inner periphery to form part of this lateral surface. A holding bracket 20 is preferably provided on the housing part 14.

In the base area 18 of the housing part 14, provision is made for an insertion opening 28 which, in the radial direction, preferably extends over the entire width of the receptacle space 16. An insertion bevel 29 is provided on a longitudinal edge of the insertion opening 28, which bevel tapers the thickness of the wall thickness of the base area 18 towards the receptacle space 16. This makes it possible to wind and unwind the winding article 15 without kinks and in a simplified manner.

At least one gripping surface 31, in particular a recessed grip, is provided on an outer side of the winding article receptacle 12. Such gripping surfaces 31 can also be provided on the outer side of the base area 18.

The gripping surfaces 31, in particular the recessed grips, can be formed having a fluorescent material or a fluorescent coating. This makes simple handling of the device 11 possible, even in darkened operating theatres. Moreover, provision can preferably be made for the body edges of the insertion opening 28, in particular the insertion bevel, to likewise additionally be composed of fluorescent material or be provided with a fluorescent coating in order to characterize the feed region of the winding article 15 to receive the latter and also characterize the removal region to remove said winding article.

The receptacle space 16 of the device 11 comprises a winding article guide 33 which enables forced guiding during the winding and unwinding process of the winding article 15. This winding article guide 33 is formed by a shaped surface 34 in the winding article receptacle 12 which points into the receptacle space 16. This shaped surface 34 is in particular designed as a grooved surface 34 and comprises an encircling groove 36, with a groove end (not illustrated in any more detail) for example being provided on the inner periphery and forming the winding start for winding the winding article 15. Alternatively, it is also possible to provide a groove end on the outer periphery of the winding article guide 33. One or more grooves 36 or turns of the winding article guide 33 can be laid as a function of the length of the winding article 15 to be wound. As a result of the insertion opening 28, one end of the winding article 15 can be acquired by turning the housing part 14 and/or the winding article receptacle 12 in each case through at least 180°; this end representing the start for unwinding the winding article. The positioning of the winding end of the winding article can be provided, for example, by a marking on the insertion opening 28 or by an elongate recess at the insertion opening 28, the contour of the elongate opening or recess being matched to the adjacent groove 36.

The groove 36 is preferably separated by webs 37 arranged in between, so that the individual turns of the winding article 15 are arranged next to one another in a plane in the receptacle space 16 and are respectively provided separately, detached from one another. In accordance with a preferred embodiment of the invention, the height of the webs 37 is dimensioned such that the diameter region of the wires to be held can be completely held in a space formed between the webs 37 and a groove bottom. This makes it possible for a distance to be formed between an end face of the web 37 and the opposite bearing surface 28 of the housing part 14 to be very small. The advantage of this is that jamming or catching in this region is prevented when holding very thin wires. The distance between the end face of the web 37 and the bearing surface 38 of the housing part 14 is preferably smaller than the smallest diameter of the winding article 15 to be held. Such a refinement makes it possible to completely arrange the winding article 15, held in the receptacle space 16, within the clear space between the webs 37 so that the wound winding article 15 is prevented or prevented to the largest possible extent from bearing on the bearing surface 38 of the housing part 14. As a result of the internal stress of the winding article 15, it respectively bears on an end face of the web delimiting the outer periphery of the respective hollow space.

According to a further preferred refinement of the device 11, provision is made for providing markings adjacent to the insertion opening 28 on an outer side of the housing part 14, which markings are provided along the insertion opening 28 from radially on the outside to radially on the inside. These markings can be provided with different colourings and/or additionally with numerical data. Preferably, the numerical data comprises length data which corresponds to the wound winding article 15. As a result, it is possible for, firstly, the region which has the starting winding location for a predetermined length of the winding article 15, in particular of the guidewire, to be marked for the user. Furthermore, the advantage of these markings is that in the case of, for example, a winding article 15 which extends along the grooves 36 over the entire receptacle space 16, the marking allows conclusions to be drawn about the amount or length of the winding article 15 removed after a partial removal of the winding article. Hence, such markings can have a two-fold use.

According to a further alternative embodiment (not illustrated in any more detail), provision can be made for the height of the webs 37 to comprise at least half the diameter of the winding article. The height of the entire receptacle space 16, that is to say from the groove floor up to the bearing surface 38, which lies opposite and is provided on the housing part 14, is less than double the diameter of the winding article. The bearing surface 38 can preferably also be formed by semi-circular lobes 39 which extend outwards in a star-shaped manner in the case of a receptacle space 16 aligned radially with respect to the axis of rotation of the device 11. By way of example, this can be seen in FIG. 4. These lobes 39 reduce the size of the bearing surface 38 of the winding article 15 located in the receptacle space 16 and reduce the friction of the housing part 14, as a result of which friction is reduced and the winding and unwinding is eased.

The winding article receptacle 12 and the housing part 14 are preferably injection-moulded parts made of plastic. As long as the device 11 is intended to be used a number of times, an autoclavable plastic is used. As a result of the only two-part design of the device 11, simple disassembly and assembly is possible in a short period of time, with the result that cleaning can also be eased.

By way of example, provision is made on the housing part 14 for a rinsing opening 49 which makes it possible for a cleaning or rinsing liquid or a lubricant to be guided into the receptacle space 16, be distributed within the receptacle space 16 and leave via the insertion opening 28 or the interface, lying radially on the outside, between the winding receptacle 12 and the housing part 14. This can likewise be a so-called Luer connection.

FIG. 5 schematically illustrates the insertion opening 28 in an enlarged fashion. This insertion opening 28 does not only extend radially along the receptacle space 16, as illustrated in FIG. 5, but also axially at least over the height of the webs 37. Furthermore, provision is preferably made for the radially outer region of the exit opening 28 to be wider than the radially inner region. The increasing opening width, as illustrated in the exemplary embodiment, can be provided by a discontinuous profile or else can comprise a continuously curved profile. The receptacle space 16 preferably has a start section 46 at the outermost end of the groove, which section extends continuously from the groove floor up to the height of the web 37. The web 37 subsequently continues helically, in order to form the receptacle space 16. When unwinding or removing the winding article 15, a free end 48 of the winding article 15 extends radially outwards from the insertion opening 28 on account of the internal stress. If the housing part 14 and the winding article receptacle 12 are twisted further, the winding article 15 is led out of the receptacle space 16 along the insertion bevel 29. First of all, an outer turn is removed from the receptacle space 16. This outer turn lies in a space formed between the web 37 and a lateral surface 19 of the housing part 18. Once this turn has been completely removed, the winding article 15 follows along the start section 46, which is continuously increasing, so that a secured winding article removal is ensured in the transition from a free space between the web 37 and the lateral surface 19 to a space between two adjacent webs 37.

FIG. 6 illustrates a perspective view of an alternative embodiment of the device 11. This alternative embodiment of the device 11 differs from the previously described embodiment in that the receptacle space 16 is aligned axially with respect to the axis of rotation 17 of the winding article receptacle 12 and of the housing part 14 of the device 11. The advantages and methods of operation of this alternative embodiment in accordance with FIG. 6 are analogous to those of the previously described embodiment. FIGS. 7a and 7b show a view of the top side and the bottom side of the alternative embodiments in accordance with FIG. 6.

As a result of the alternative arrangement of the receptacle space 16, the winding article receptacle 12 is in the form of a ring, for example, which for example has a U-shaped cross section, as illustrated in a full cross section in FIG. 8. The winding article guide 33, in particular the shaped surface 34, is provided on the radial outer limb of the U-shaped cross section of the winding article receptacle 12. A peripheral recess 42 is for example provided on the radial inner limb of the U-shaped cross section of the winding article receptacle 12, into which recess at least one latching element 23, positioned on the housing part 14, engages. The recess 42 and the at least one latching element 23 form the detachable latching connection 22 in an exemplary manner. The latching element 23 can also be designed as a radially encircling projection. Alternatively, the projection can only extend above the periphery in sections. The housing part 14 can be latched onto the winding article receptacle 12 by means of a simple clip-on connection. Such an arrangement can also be disassembled easily.

The insertion opening 28 is provided on an outer lateral surface 19 of the housing part 14 and extends in the lateral surface 19 in the axial direction. The width of the insertion opening 28 is such that independent unthreading results due to internal stress when the housing parts 12, 14 are turned.

The insertion opening 28 can have an elongate opening section which can for example constitute an unthreading aid in order to simplify the removal of one end of the winding article 15 from the wound position in the receptacle space 16 as a result of its inherent stiffness.

By way of example, in accordance with FIG. 7a and FIG. 7b, the winding article receptacle 12 comprises two gripping surfaces, designed as recessed grips 31, which interrupt the U-shaped cross section. Constrictions of the U-shaped cross section can also be provided as an alternative to such recessed grips. The advantage of the arrangement illustrated in FIG. 7a and FIG. 7b is that a device 11 is created which is very light in terms of weight.

In order to minimize the bearing surface 38 in the receptacle space 16, lobes 39, in particular semi-circular lobes, are preferably provided on the housing part 14, as illustrated by way of example in FIG. 9. These semi-circular lobes 39 extend transversely with respect to the shaped, in particular grooved, surface 34 which has a continuous groove 36 in the form of a helical thread. Such semi-circular lobes 39 are provided at regular intervals at a distance from the inner periphery of the lateral surface 19 of the housing part 14.

Moreover, an opening or a connection for rinsing the receptacle space 16 can be provided on the lateral surface 19 of the housing part 14. To this end, provision is made in particular for a so-called Luer connection. This makes it possible to rinse and clean the receptacle space in the wound state of the winding article 15. Such a Luer connection can also be provided in the embodiments in accordance with FIGS. 1 to 5.

The embodiment of the dispenser 11 illustrated in FIG. 6 is also preferably only of a two-part design, with the winding article receptacle 12 and the housing part 14 in particular being designed as injection-moulded parts.

FIG. 10 illustrates, in a perspective view, an apparatus 51 for winding an elastically deformable winding article 15, by means of which the winding article 15 can be wound into the device 11. This apparatus 11 for automatically winding in particular flexible endoscopic instruments, such as guidewires, catheters, loops, biopsy forceps or the like, comprises a housing 52 in which a drive device (not illustrated in any more detail) is provided. This drive device comprises a control and a motor, in particular a servomotor. This servomotor drives a rotation device 54 which, by way of example, comprises a rotary plate 55 which preferably is part of a receptacle recess 56 adjacent to a top side of the housing 52. The rotary plate 55 is integrated into the receptacle recess 56 in such a fashion that provision is preferably made for a closed housing surface. The receptacle recess 56 is preferably matched to the outer contour of the device 11. By way of example, provision can be made for a cut-out 57 for holding the holding bracket 20. This results in an anti-twist protection for the housing part 14 after the device 11 has been placed into the receptacle recess 56, or vice versa, for a subsequent winding process, in which the winding receptacle 12 is rotationally driven.

For the purposes of automatic winding, provision is made for the device 11 to be placed into the receptacle recess 56. In the process, catches 58, which protrude upwards compared to the rotary plate 55, preferably engage into gripping surfaces 31 or recesses of the winding receptacle 12. By way of example, the housing part 14 is provided in the receptacle recess 56 in a manner secured against twisting by means of the holding bracket 20. Locks 68, which for example protrude laterally into the receptacle recess 56, fix the device 11 in the receptacle recess 56. The apparatus 51 is switched on and off by means of a switch 60. A potentiometer 61 can be used to set the winding speed, for example. A further potentiometer 62 can be used to set the winding duration, for example, as a function of the length of the winding article 15 to be wound. A display 63 can be used to output various items of information for the user, such as the information that the apparatus 51 is ready to start a winding process or that the winding process has now been completed.

The winding process is started after inserting the device 11 into the apparatus 51 by means of a pushbutton 65, for example, which is preferably designed as a pedal switch. A start and stop button can also be provided on the housing 52.

A slow start-up of the rotary plate 55 is preferably effected at the start of the winding process so that, for example, a single or one and a half-fold, but also two-fold or three-fold, rotation is effected at a slower or slowly increasing speed in order to ensure that the start of the winding article 15 is held and pulled in. Subsequently, a number of turns can be wound at a high drive speed, depending on the length of the winding article 15. The last winding is preferably again driven at a reducing winding speed. A servomotor is preferably provided for this actuation, which servomotor can directly drive an axis of rotation of the rotary plate 15. Alternatively, it is also possible for a gearbox to be provided switched in between. It is likewise possible to utilize belt drives or any other type of drive in order to preferably obtain a flat compact housing 52 of the apparatus 51.

Setting the winding length by means of the potentiometer 62 affords the possibility of, for example, pushing the pushbutton 65 at the start of the winding process and subsequently effecting automatic and complete winding without further actuation of switches or pushbuttons being required. Once the rotation device 54 has effected the required number of rotations, the control recognizes that the winding process has been completed and stops the rotation device 54.

During the winding process, an operator can align the winding article 15 with respect to the insertion opening 28. Alternatively, provision can be made on the housing 52 for a feed device which guides the winding article 15. In particular, provision in this case is made for the feed device to move radially outwards with increasing winding so that the feed of the winding article 15 is always positioned in accordance with the subsequent groove 36 of the winding receptacle 15. The winding article 15 can also be simultaneously cleaned in the process.

The apparatus 51 preferably has an optical signalling device 67 which directs laser light, for example, onto the insertion opening 28 of the receptacle space 16 of the device 11. This optical signalling device 67 can specify the insertion position of the winding article 15 for winding the winding article 15. By way of example, in the case of a 4 m or 4.5 m long guidewire, the winding start is provided on a radial inner side of the insertion opening 28. In the case of a length of, for example, 2 m or 2.5 m, the starting point is in the central region of the insertion opening 28. This position can be displayed in a precise fashion by the laser light.

Once the winding process is complete, the device 11 is taken out of the receptacle recess 56. In the process, provision can be made for, for example, one or more recessed grips to adjoin the cut-out 57 or the receptacle recess 56 in order to remove the device 11. Such cut-outs are provided adjacently to detachable locks 68 which are provided radially around the receptacle recess 56 and are preferably distributed evenly around the periphery of the latter in order to hold down the device 11 during the winding process. Such locks 18 can be designed as resilient latching elements or the like, which engage on the housing part 14 in order to secure the winding position. As an alternative to the cut-outs, or in addition thereto, provision can be made for ejector elements which can be actuated by the pushbutton 65 or a separate switch. Such ejector elements can preferably be integrated in the catches 58 or can be formed by the catches 58. They are moved upwards to eject the device 11 so that subsequently the device 11 is freed from the locks 68 and can be removed. Likewise, it is possible for provision to be made for such ejector elements to separately be integrated in the rotary plate 55 or in the receptacle recess 56.

The receptacle recess 56 illustrated in FIG. 10 is arranged at a distance from the respective side edges of the housing 52. This apparatus 51 is provided in particular for winding a device in accordance with FIGS. 1 to 5. As an alternative to designing a receptacle recess 56, it is also possible to provide a different type of receptacle which has the same functions as the receptacle recess 56 and the rotation device 54. By way of example, this arrangement can also be provided in a raised fashion compared to a housing surface; in this case provision having to be made for appropriate provisions to form an anti-twist protection and to keep the device 11 down against the rotation device 54.

In principle, this apparatus 51 is also suitable for winding the alternative embodiment of the device 11 in accordance with FIGS. 6 to 9. In this case, provision can be made for the receptacle recess 56 to be adjacent to a side wall of the housing 52 so that the end-face insertion opening 28 of the device 11 in accordance with FIGS. 6 to 9 is accessible. Alternatively, it is also possible that a type of cage is provided which extends upwards with respect to the rotation device 54 in order to engage on the housing part 14, this cage having at least one lateral opening so that the lateral insertion opening 28 of the device 11, as can be seen in FIG. 6, is accessible to the winding article 15. All further features and functions of the apparatus 51 are the same for the embodiment of the device in accordance with FIGS. 6 to 9 as for the embodiment in accordance with FIGS. 1 to 5.

The invention claimed is:

1. Device for holding an elastically deformable winding article, in particular a flexible medical instrument such as a medical guidewire or a catheter, the device comprising:
   a receptacle space for receiving the winding article,
   a winding article receptacle and a housing part, which housing part is covering the winding article receptacle at least in parts, and the receptacle space is formed in between the winding article receptacle and the housing part,
   the winding article receptacle and the housing part are connected to one another such that the winding article receptacle and the housing part are twistable relative to each other about an axis of rotation,
   the winding article receptacle further comprising a winding article guide which winding article guide arranges a number of turns of the winding article next to each for receiving the winding article,
   the winding article guide for holding the turns of the winding article arranged next to one another is aligned radially with respect to the axis of rotation of the winding article receptacle,
   the winding article guide is formed by a shaped surface, which comprises an encircling groove, and
   an insertion opening leading to the receptacle space is provided in the housing part, which extends in radial direction over the entire width of the receptacle space.

2. Device according to claim 1, wherein the encircling groove has a groove depth which corresponds to at least half of the winding article diameter of the winding article to be held.

3. Device according to claim 1, wherein a distance between a bearing surface of the housing part and an end surface of the encircling groove is designed to be smaller than, in terms of diameter, the smallest winding article to be held, or to be smaller than half the diameter of the smallest winding article to be held.

4. Device according to claim 1, wherein an effective height of the receptacle space is smaller than twice the diameter of the winding article to be held.

5. Device according to claim 1, wherein the insertion opening has an insertion bevel pointing towards the receptacle space.

6. Device according to claim 1, wherein provision is made for a bearing surface which lies opposite the shaped surface in the receptacle space, is aligned transversely with respect to the shaped surface.

7. Device according to claim 6, wherein the bearing surface is formed by semi-circular lobes.

8. Device according to claim 1, wherein the winding article receptacle and the housing part are connected to one another such that they are turnable by means of a detachable latching connection.

9. Device according to claim 8, wherein the means of the detachable latching connection has at least one latching element which is designed to resiliently yield and which is formed onto the winding article receptacle or the housing part.

10. Device according to claim 1, wherein at least one gripping surface is provided on the housing part, the winding article receptacle or the housing part and the winding article receptacle.

11. Device according to claim 1, wherein a Luer connection or a rinsing opening is provided on the winding article receptacle or the housing part.

* * * * *